United States Patent [19]

Beller et al.

[11] Patent Number: 5,569,776

[45] Date of Patent: Oct. 29, 1996

[54] PROCESS FOR THE PREPARATION OF 4-FLUOROALKOXYCINNAMONITRILES

[75] Inventors: Matthias Beller, Niedernhausen; Klaus Forstinger, Kelsterbach, both of Germany

[73] Assignee: Hoechet AG, Germany

[21] Appl. No.: 400,976

[22] Filed: Mar. 8, 1995

[30] Foreign Application Priority Data

Mar. 10, 1994 [DE] Germany ............... 44 08 083.2

[51] Int. Cl.⁶ .................................. C07C 255/07
[52] U.S. Cl. .............................. 558/373; 558/374
[58] Field of Search ...................... 558/373, 374

[56] References Cited

U.S. PATENT DOCUMENTS

| | | | |
|---|---|---|---|
| 2,583,194 | 1/1952 | Weisler | 558/373 X |
| 3,636,073 | 1/1972 | Cragoe, Jr. et al. | 558/374 X |
| 4,235,805 | 11/1980 | Lenselink | 558/374 X |
| 4,755,615 | 7/1988 | Kaufhold et al. | 558/374 |

FOREIGN PATENT DOCUMENTS

| | | |
|---|---|---|
| 0174769 | 3/1986 | European Pat. Off. |
| 4408083 | 1/1995 | Germany |

OTHER PUBLICATIONS

Weygand/Hilgetag, Preparative Organic Chemistry (1972), John Wiley & Sons; pp. 361–367 and 983–986.

Journal of Organic Chemistry, vol. 48, "Aromatic Fluoroalkoxylation via Direct Aromatic Nucleophilic Substitution", pp. 3771–3773 (1983).

Chemische Berichte, vol. 95, "Substituenteneinflüsse bei der Reiktion aromatischer Aldehyde mit Cyanessigsäure", pp. 967–970 (1962).

Primary Examiner—Joseph McKane
Attorney, Agent, or Firm—Connolly & Hutz

[57] ABSTRACT

Process for the preparation of 4-fluoroalkoxycinnamonitriles.

The invention relates to a process for the preparation of fluoroalkoxycinnamonitriles of the formula (I)

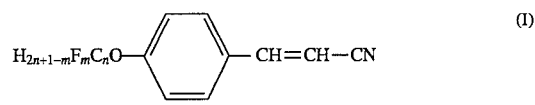

in which n is 1 to 8 and m is 1 to 17, where $m \leq 2n+1$, by reacting 4-fluorobenzaldehyde with a fluoroalkanol of the formula (II)

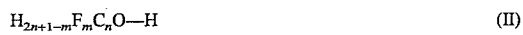

in which m and n are as defined above, in the presence of a base and, if appropriate, a solvent, and reacting the resulting 4-fluoroalkoxybenzaldehyde with cyanoacetic acid or an alkyl cyanoacetate in the presence of a base and, if appropriate, a solvent.

20 Claims, No Drawings

PROCESS FOR THE PREPARATION OF 4-FLUOROALKOXYCINNAMONITRILES

DESCRIPTION

Process for the preparation of 4-fluoroalkoxycinnamonitriles

The present invention relates to a novel process for the preparation of 4-fluoroalkoxycinnamonitriles.

4-fluoroalkoxycinnamonitriles are important from the technical point of view as an intermediate in pharmacology. They are important, in particular, as starting material for antimycotics (ICI-D0870, Drugs of the Future, 18 (5), 424–427).

Prior-art syntheses of 4-fluoroalkoxycinnamonitriles start, for example, from p-chlorobenzonitrile, which is reacted, in a first reaction step, with 2,2,3,3'tetra-fluoropropanol to give 4-(2,2,3,3-tetrafluoropropoxy)benzonitrile (EP 0 472 392). This reaction has already been described by J. P. Idoux (J. Org. Chem. 48, 3772, 1983). In a second reaction step, 4-(2,2,3,3-tetrafluoropropoxy)benzonitrile is reacted in the presence of metal hydrides, such as diisobutylaluminumhydride, to give the corresponding benzaldehyde (JPS Sho 61-72767). 4-(2,2,3,3-tetrafluoropropoxy)-benzaldehyde subsequently reacts with diethyl ethoxycarbonylmethanephosphonate to give ethyl 4-(2,2,3,3-tetrafluoropropoxy-)cinnamate, which is hydrolyzed, in a fourth step, to give free cinnamic acid. The fifth reaction step consists in the formation of the cinnamoyl chloride, which, in a sixth reaction step, reacts with aqueous ammonia to give 4-(2,2,3,3-tetrafluoropropoxy) cinnamamide. In the seventh and last step of the reaction sequence, the abovementioned cinnamamide is reacted in the presence of thionyl chloride or phosphorus pentachloride to give the desired product.

The method described in EP 0 472 392 for the preparation of 4-(2,2,3,3-tetrafluoropropoxy) cinnamonitrile in seven reaction steps is unsuitable for the industrial preparation of substantial amounts of the product. The shortcomings of this process are, in particular, the low total yield of the product desired, and the high number of steps, in which many by-products, salt residues and solvent residues are produced. Another problem is the use of very expensive reagents such as metal hydrides and ethoxycarbonylmethylphosphonates. Moreover, the use of metal hydrides requires particular safety measures when carrying out the process on an industrial scale.

EP 174 769 describes the synthesis of the analogous 4-trifluoromethoxycinnamonitrile starting from 4-trifluoromethoxyaniline, which is in succession diazotized, iodized, and subsequently stoichiometrically lithiized. Reaction of the sensitive aryllithium reagent with dimethylformamide affords 4-trifluoromethoxybenzaldehyde, which together with diethyl 1-cyanomethylphosphonate affords the desired 4-trifluoromethoxycinnamonitrile.

The disadvantages of the process described in EP 174 769 are similar to those of the process described in EP 0 472 392. The large number of steps and the correspondingly low total yield as well as the problems with using stoichiometric amounts of organometal compounds and toxic cyanomethylphosphonates make the process unsuitable for scaling-up to an industrial scale.

There was therefore a great demand for making accessible 4-fluoroalkoxycinnamonitriles in a simple manner for scaling-up to an industrial scale.

This aim is achieved by a process for the preparation of 4-fluoroalkoxycinnamonitriles of the formula (I)

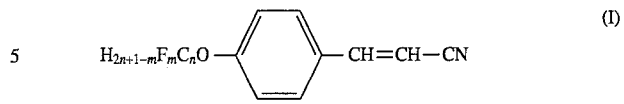

in which n is 1 to 8 and m is 1 to 17, where $m \leq 2n+1$, which comprises reacting 4-fluorobenzaldehyde with a fluoroalkanol of the formula (II)

in which m and n are as defined above, in the presence of a base and, if appropriate, a solvent, and reacting the resulting 4-fluoroalkoxybenzaldehyde with cyanoacetic acid or an alkyl cyanoacetate in the presence of a base and, if appropriate, a solvent.

The process is highly important for the preparation of compounds of the formula (I) in which n is 1 to 4 and m is 2 to 9.

The preparation of 4-(2,2,3,3-tetrafluoropropoxy) cinnamonitrile, 4-trifluoromethoxycinnamonitrile, 4-octafluoropentoxycinnamonitrile or 4-dodecafluoroheptoxycinnamonitrile is furthermore of particular interest.

The process is also highly suitable for the preparation of partially fluorinated 4-fluoroalkoxycinnamonitriles of the formula (I), where $m<2n+1$.

The process according to the invention is carried out as follows:

4-fluorobenzaldehyde together with the fluoroalkanol is reacted in the presence of 0.5 to 3, in particular 0.6 to 1.25, base equivalents at temperatures of between 10° C. and 180° C., in particular 60° to 155° C., to give 4-fluoroalkoxybenzaldehyde. Suitable as the base are, for example, alkali metal carbonates, in particular potassium carbonate, sodium carbonate or mixtures of potassium carbonate and sodium carbonate. The reaction can be carried out in the presence of dipolar aprotic solvents, such as N,N-dimethylacetamide, sulfolane and N,N-dimethylformamide, but also without solvents. In the latter case, it is advantageous to carry out the process in an excess of fluoroalkanol which thus acts as a solvent. The amount of fluoroalkanol to be employed will depend on the amount of base employed and is to be selected such that the reaction mixture remains stirrable, and is advantageously 0.8 to 1.5 equivalents based on 4-fluorobenzaldehyde employed.

The process according to the invention can be carried out as a partial reaction, but also, preferably, as a largely complete reaction based on in each case one of the two starting materials (4-fluorobenzaldehyde or fluoroalkanol), preferably 4-fluorobenzaldehyde. In the case of a partial reaction, the valuable starting materials are recovered by means of distillation. In the case of complete reaction, the educt employed in excess is equally recovered by means of distillation.

Two routes are suitable for work-up:
1) Salts (excess base and base fluoride formed) present in the reaction mixture are separated off by filtration. The product is subsequently distilled off from the filtrate.
2) Alternatively, it is possible to dissolve the base fluoride formed and excess salt by adding water, to separate the phases formed, and either to use the product found in the organic phase directly in the subsequent reaction or, if required, to purify by means of distillation. Product found in the aqueous phase can be extracted using solvents such as toluene, chlorobenzene, dichlorobenzene, methylene chloride or tert.-butyl methyl ether.

The yields of 4-fluoroalkoxybenzaldehyde by the above process are 60% to 95%.

The 4-fluoroalkoxybenzaldehyde obtained is reacted according to the invention with 0.3 to 4 equivalents, in particular with 0.6 to 2.0 equivalents, preferably 0.8 to 1.2 equivalents, of cyanoacetic acid or alkyl cyanoacetates at temperatures from 50° to 250° C., preferably 80° to 180° C., in the presence of a base or a basic catalyst to give 4-fluoroalkoxycinnamonitrile.

Methyl cyanoacetate, ethyl cyanoacetate and propyl cyanoacetate have proved to be advantageous alkyl cyanoacetates. Bases or basic catalysts which can be employed are aromatic and aliphatic amines, alkali metal carbonates and alkaline earth metal carbonates, or basic oxides and hydroxides, such as NaOH, KOH or $Al_2O_3$.

In many cases, amines such as pyridine, piperidine, morpholine, tri-butylamine, triethylamine, tripropylamine, benzylamine, aniline and dialkylaniline, have proved themselves as base and, if appropriate, also as solvent.

The reaction according to the invention with cyanoacetic acid derivatives can be carried out in the absence of solvents. However, it may be advantageous to carry out the process in the presence of solvents. Examples of substances which can act as solvents are aromatics, such as benzene, toluene, xylenes, dipolar aprotic solvents, such as dimethylformamide, dimethylacetamide, dimethyl sulfoxide, sulfolane, alcohols, such as ethanol, propanol, butanol, glyme, or ethers, such as diglyme. The amount of solvent is 5 to 90% by weight, based on the 4-fluoroalkoxybenzaldehyde employed.

The reaction can be carried out continuously or batchwise. Under some circumstances, it may be advantageous to meter in cyanoacetic acid or alkyl cyanoacetate, or to meter in more cyanoacetic acid or alkyl cyanoacetate, during the reaction. When the reaction has ended, the reaction mixture is cooled and the product isolated.

The crude product can be purified by distillation or recrystallization.

As a rule, the products obtained are in the form of mixtures of cis and trans isomers with regard to the double bond. However, it is possible to alter the isomeric ratio under specific conditions, thus, for example, it being possible to preferentially produce one of the isomers by means of prolonged heating or by crystallization.

In principle, the base or the base catalyst can be employed in homogeneous or else heterogenous form.

Under some circumstances, it is advantageous to carry out the reaction in a multi-phase system.

The novel two-step process is markedly superior to the process described in EP 0 472 392 and EP 174 769 since the product is obtained in only two reaction steps compared with seven steps and 5 steps, respectively. The total yield of 4-fluoroalkoxycinnamonitrile obtained by the process according to the invention is approximately 80% and is therefore markedly improved in comparison with EP 0 472 392. By virtue of this, the process according to the invention is markedly superior to the old, prior-art process from an economical and ecological point of view.

The examples which follow are intended to illustrate the process according to the invention without imposing any limitation thereto.

EXAMPLE 1

103.7 g of potassium carbonate, 198.0 g of 2,2,3,3-tetrafluoropropanol and 124 g of 4-fluorobenzaldehyde are heated for 20 hours at 140° C. The boiling point of the reaction mixture is first 125° C. As the reaction progresses, the internal temperature rises to 140° C. The mixture is then cooled to 100° C., and excess 2,2,3,3-tetrafluoropropanol is distilled in vacuo. The reaction mixture is cooled to room temperature, 375 g of water are then added, and the phases are separated. This gives 283.8 g of a yellowish, aqueous suspension containing 17% of water and 80% of tetrafluoropropoxybenzaldehyde. The purity of the tetrafluoropropoxybenzaldehyde is 98%. The moist product is directly processed.

Yield: 227 g of 4-(2,2,3,3)-tetrafluoropropoxybenzaldehyde 98% pure=222.5 g 100% pure=94%.

EXAMPLE 2

165.8 g of potassium carbonate, 198.0 g of 2,2,3,3-tetrafluoropropanol and 124 g of 4-fluorobenzaldehyde are heated for 20 hours at 140° C. The boiling point of the reaction mixture is first 125° C. As the reaction progresses, the internal temperature rises to 145° C.

61 g of starting material are subsequently distilled off at 45 mm Hg, a bottom temperature of 130° C. and a head temperature of 55° C. After the mixture has been cooled to room temperature, 600 ml of water are added. The phase separation gives 256.1 g of product containing 82.5% of 4-(2,2,3,3)-tetrafluoropropoxybenzaldehyde (purity: 97.5 %) (water content 14.4%).

Yield: 89.5%.

EXAMPLE 3

500 ml of dimethylacetamide, 304 g of potassium carbonate, 248 g of 4-fluorobenzaldehyde and 290 g of 2,2,3,3-tetrafluoropropanol are heated for 22.5 hours at 140° C. The reaction mixture is subsequently cooled to 20° C. and filtered. The salt mixture is washed using 300 ml of dimethylacetamide. After the filtrate has been distilled in vacuo at 3 mbar, a bottom temperature of 135° C. and a head temperature of 109° C. to 110° C., 387.95 g of 4-(2,2,3,3-tetrafluoropropoxy) benzaldehyde with a purity (GC) of 98% to 99% are obtained.

Yield: 80.5%.

EXAMPLE 4

138.2 g of potassium carbonate, 21.2 g of sodium carbonate, 198 g of tetrafluoropropanol and 124 g of 4-fluorobenzaldehyde are introduced at room temperature under argon protective gas and heated for 20 hours at 140° C. The boiling point of the reaction mixture is initially 125° C. As the reaction progresses, the internal temperature rises to 140° C. After 20 hours, the mixture is cooled to 25° C and filtered. This gives 229.6 g of filtrate containing 72% of 4-(2,2,3,3-tetrafluoropropoxy)benzaldehyde. The filter cake is washed 3 times using in each case 100 ml of toluene. Filtrate and toluene used for washing are collected separately. After 63.9 g of 2,2,3,3-tetrafluoropropanol have been distilled off from the filtrate, the distillation residue is combined with the toluene used for washing. After the toluene has been distilled off under atmospheric pressure, the residue is fractionated in vacuo at 3 mbar and a bottom temperature of up to 135° C. and a head temperature of 109° C. to 110° C. As the main fraction, 188.7 g of 4-(2,2,3,3-tetrafluoropropoxy)benzaldehyde with a purity (GC) of 98% to 99% are obtained.

Yield: 79.9%.

EXAMPLE 5

82.9 g of potassium carbonate, 63.6 g of sodium carbonate, 198 g of tetrafluoropropanol and 124 g of 4-fluorobenzaldehyde are introduced at room temperature under argon protective gas and heated for 20 hours at 120° C. After 20 hours, the mixture is cooled to 25° C. 99.3 g of high-boiling components (approximately 16% by weight of 4-fluorobenzaldehyde, 75.6% of 2,2,3,3-tetrafluoropropanol) are subsequently distilled off at 20 to 30 mbar and a bottom temperature of up to 115° C. 50 ml of toluene are added to the bulb residue, and the mixture is filtered. The salt is washed using 50 ml of toluene. The toluene used for washing is combined with the filtrate. After the toluene has been distilled off under atmospheric pressure, the residue is fractionated in vacuo at 3 mbar, a bottom temperature of up to 135° C. and a head temperature of 109° C. to 110° C. This gives 15 g of 4-fluorobenzaldehyde, and, as the main fraction, 185.4 g of 4-(2,2,3,3-tetrafluoropropoxy)benzaldehyde with a purity (GC) of 98% to 99%.

Yield: 88.7%.

EXAMPLE 6

82.9 g of potassium carbonate, 63.6 g of sodium carbonate, 198 g of tetrafluoropropanol, 124 g of 4-fluorobenzaldehyde and 500 ml of N-methylpyrrolidone (NMP) are introduced at room temperature under argon protective gas (slightly exothermal) and heated for 20 hours at 120° C. After 20 hours, the mixture is cooled to 25° C., and salt is filtered off. The salt is washed with a small amount of NMP. Fractional distillation allows 187.5 g of 4-(2,2,3,3-tetrafluoropropoxy)benzaldehyde of a purity (GC) of 98% to be isolated from the NMP solution, which contains approximately 25% by weight of product.

Yield: 79.4%.

EXAMPLE 7

36.3 g of potassium carbonate, 41.3 g of octafluoropentanol and 33 g of 4-fluorobenzaldehyde are introduced at room temperature into a 250 ml 2-necked flask. The mixture subsequently is heated at 140° C. and stirred for 29 hours at 140° C. After the mixture has been cooled to room temperature, it is filtered. The filter residue is washed twice using 100 ml of toluene. The filtrate and toluene used for washing are combined and fractionated. 53 g of octafluoropentoxybenzaldehyde with a purity of 99.5% are obtained.

Yield: 88%.

EXAMPLE 8

100.0 g of 4-(2,2,3,3-tetrafluoropropoxy)benzaldehyde and 36.6 g of cyanoacetic acid are refluxed for 1 hour in a mixture of 50 ml of pyridine and 50 ml of piperidine. A further 4.0 g of cyanoacetic acid are then added, and heating is continued for 15 minutes. After the reaction mixture has cooled, it is distilled in vacuo. This gives 93.03 g of the desired product 4-(2,2,3,3-tetrafluoropropoxy) cinnamonitrile as a cis/trans mixture.

Yield: 85% of 4-(2,2,3,3-tetrafluoropropoxy) cinnamonitrile.

EXAMPLE 9

30.0 g of 4-(2,2,3,3-tetrafluoropropoxy)benzaldehyde and 15.3 g of cyanoacetic acid are heated for 4 hours in 60 ml of piperidine at an oil-bath temperature of 110° C. After the reaction mixture has been cooled, it is distilled in vacuo. This gives 24.1 g of the desired product 4-(2,2,3,3-tetrafluoropropoxy)cinnamonitrile as a cis/trans mixture.

Yield: 74% of 4-(2,2,3,3-tetrafluoropropoxy) cinnamonitrile.

EXAMPLE 10

50.0 g of 4-(2,2,3,3-tetrafluoropropoxy)benzaldehyde and 18.0 g of cyanoacetic acid are refluxed for 24 hours in a mixture of 60 ml of pyridine and 5 ml of piperidine. After the reaction mixture has been cooled, it is distilled in vacuo. This gives 33.93 g of the desired product 4-(2,2,3,3-tetrafluoropropoxy) cinnamonitrile.

Yield: 62% of 4-(2,2,3,3-tetrafluoropropoxy)cinnamonitrile.

EXAMPLE 11

500.0 g of 4-(2,2,3,3-tetrafluoropropoxy)benzaldehyde and 183 g of cyanoacetic acid are heated for 1 hour at 110° C. in a mixture of 250 ml of pyridine and 250 ml of piperidine. A further 36.6 g of cyanoacetic acid are then added and heating is continued for 30 minutes. After the reaction mixture has been cooled, it is distilled in vacuo. 433.1 g of the desired product 4-(2,2,3,3-tetrafluoropropoxy) cinnamonitrile are obtained as a cis/trans mixture.

Yield: 78% of 4-(2,2,3,3-tetrafluoropropoxy) cinnamonitrile.

EXAMPLE 12

30 g of 4-(2,2,3,3-tetrafluoropropoxy)benzaldehyde and 11 g of cyanoacetic acid are heated for 30 minutes at 110° C. in a mixture of 50 ml of toluene, 10 ml of pyridine and 10 ml of piperidine. A further 2.2 g of cyanoacetic acid are subsequently added and heating is continued for 30 minutes. After the mixture has been cooled to room temperature, the crude product is recrystallized from ethyl acetate. This gives 33 g of 4-(2,2,3,3-tetrafluoropropoxy) cinnamonitrile (90% pure)

Yield: 90% of 4-(2,2,3,3-tetrafluoropropoxy) cinnamonitrile.

We claim:

1. A process for the preparation of fluoroalkoxycinnamonitriles of the formula (I)

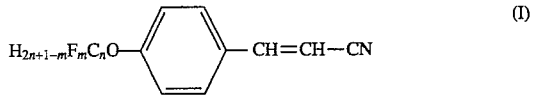

in which n is 1 to 8 and m is 1 to 17, where $m \leq 2n+1$, which comprises reacting 4-fluorobenzaldehyde with a fluoroalkanol of the formula (II)

in which m and n are as defined above, in the presence of a base and, optionally a solvent, and reacting the resulting 4-fluoroalkoxybenzaldehyde with cyanoacetic acid or an alkyl cyanoacetate in the presence of a base and, optionally a solvent.

2. A process as claimed in claim 1, wherein n is 1 to 4 and m is 2 to 9.

3. A process as claimed in claim 1, wherein 4-(2,2,3,3-tetrafluoropropoxy)cinnamonitrile, 4-trifluoromethoxycinnamonitrile, 4-octafluoropentoxycinnamonitrile or 4-dodecafluoroheptoxycinnamonitrile are prepared.

4. A process as claimed in claim 1, wherein m<2n+1.

5. A process as claimed in claim 1, wherein the reaction of the fluoroalkanol of the formula (II) with 4-fluorobenzaldehyde is carded out in the presence of 0.5 to 3.0 base equivalents at temperatures from 10° C. to 180° C.

6. A process as claimed in claim 1, wherein an alkali metal carbonate is employed as the base for the reaction of the fluoroalkanol with 4-fluorobenzaldehyde.

7. A process as claimed in claim 1, wherein the reaction of 4-fluorobenzaldehyde with fluoroalkanol is carded out in the presence of a dipolar aprotic solvent.

8. A process as claimed in claim 1, wherein the reaction of 4-fluorobenzaldehyde with the fluoroalkanol is carried out in an excess of fluoroalkanol as the solvent.

9. A process as claimed in claim 1, wherein 4-fluoroalkoxybenzaldehyde is reacted with 0.3 to 4 equivalents of cyanoacetic acid or alkyl cyanoacetate at temperatures from 50° C. to 250° C.

10. A process as claimed in claim 1, wherein the reaction of 4-fluoroalkoxybenzaldehyde with cyanoacetic acid or alkyl cyanoacetate is carried out in the presence of an aromatic, dipolar aprotic or protic solvent.

11. A process as claimed in claim 10, wherein the aromatic solvent employed is benzene, xylene or toluene, the dipolar aprotic solvent employed is dimethylformamide, dimethylacetamide, dimethyl sulfoxide or sulfolane, and the protic solvent employed is ethanol, propanol, butanol or glyme.

12. A process as claimed in claim 10, wherein 5 to 90% by weight of solvent, based on 4-fluoroalkoxybenzaldehyde, are employed.

13. A process as claimed in claim 1, wherein the reaction of 4-fluoroalkoxybenzaldehyde with cyanoacetic acid or alkyl cyanoacetate is carried out without solvent or in the base as the solvent.

14. A process as claimed in claim 1, wherein the base employed for the reaction of 4-fluoroalkoxybenzaldehyde with cyanoacetic acid or alkyl cyanoacetate is an amine.

15. A process as claimed in claim 1, wherein the alkyl cyanoacetate employed is methyl cyanoacetate, ethyl cyanoacetate or propyl cyanoacetate.

16. The process as claimed in claim 5, wherein the reaction of the fluoroalkanol of the formula (II) with 4-fluorobenzaldehyde is carried out in the presence of 0.6 to 1.25 base equivalents at temperatures from 60° to 155° C.

17. The process as claimed in claim 6, wherein said alkali metal carbonate is potassium carbonate, sodium carbonate or a mixture of sodium carbonate and potassium carbonate.

18. The process as claimed in claim 7, wherein said dipolar aprotic solvent is N,N-dimethylacetamide, sulfolane or N,N-dimethylformamide.

19. The process as claimed in claim 9, wherein 4-fluoroalkoxybenzaldehyde is reacted with 0.6 to 2.0 equivalents of cyanoacetic acid or alkyl cyanoacetate at temperatures from 80° C. to 180° C.

20. The process as claimed in claim 19, wherein 4-fluoroalkoxybenzaldehyde is reacted with 0.8 to 1.2 equivalents of cyanoacetic acid or alkyl cyanoacetate and said base employed in the reaction is pyridine, piperidine, morpholine, tri-butylamine, triethylamine, tripropylamine, benzylamine, aniline or dialkylaniline, or a mixture of these.

* * * * *